US009867925B2

(12) United States Patent
Lyons et al.

(10) Patent No.: US 9,867,925 B2
(45) Date of Patent: Jan. 16, 2018

(54) CATHETER/FISTULA NEEDLE TO BLOODLINE CONNECTION ASSURANCE DEVICE (71) Applicants: Baxter International Inc., Deerfield, IL (US); Baxter Healthcare S.A., Glattpark (Opfikon) (CH)

(72) Inventors: Bernard J. Lyons, Evanston, IL (US); Shincy J. Maliekkal, Glenview, IL (US); William Patrick Burns, Channahon, IL (US); Justin Belanger Rohde, Des Plaines, IL (US); Serhan Acikgoz, Des Plaines, IL (US); Roshni S. Barot, Hoffman Estates, IL (US); Yuanpang S. Ding, Libertyville, IL (US); Brian Connell, Evanston, IL (US); William R. Griswold, Bristol, WI (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 584 days.

(21) Appl. No.: 14/099,503

(22) Filed: Dec. 6, 2013

(65) Prior Publication Data
US 2014/0100547 A1 Apr. 10, 2014

Related U.S. Application Data (62) Division of application No. 12/640,696, filed on Dec. 17, 2009, now Pat. No. 8,603,022.
(Continued)

(51) Int. Cl.
*A61M 37/00* (2006.01)
*A61M 1/36* (2006.01)
(Continued)

(52) U.S. Cl.
CPC ...... *A61M 1/3653* (2013.01); *A61M 39/1011* (2013.01); *A61M 39/162* (2013.01)

(58) Field of Classification Search
CPC .......... A61M 39/10; A61M 39/1011–39/1055; A61M 2039/1061–2039/1094; A61M 39/162; A61M 39/365; A61M 2039/10943
(Continued)

(56) References Cited

U.S. PATENT DOCUMENTS 3,456,965 A  7/1969  Gajewski et al.
3,479,069 A  11/1969  Sedam
(Continued)

FOREIGN PATENT DOCUMENTS

EP  183396  4/1986
EP  0695556  7/1996
(Continued)

OTHER PUBLICATIONS

International Preliminary Report on Patentability for International Application No. PCT/US2009/068760, dated Mar. 31, 2011.
(Continued)

*Primary Examiner* — Philip R West
(74) *Attorney, Agent, or Firm* — K&L Gates LLP (57) ABSTRACT In general, multiple embodiments of a catheter/fistula needle to bloodline connection assurance device, which secures and strengthens a connection between an extension tube end of a catheter or fistula needle and a bloodline, are provided. In one embodiment, the assurance device includes a clamshell having two halves that open rotatably about at least one hinge. The assurance device includes a male luer portion that pressure seals to the male luer portion of the bloodline connector. The bloodline male luer portion of the device extends to a female luer portion, which is lined with a compressible material that conforms around any industrial
(Continued)

catheter/fistula needle connector when the assurance device is closed about the mated connectors. Once the assurance device is closed, this prevents axial movement of the bloodline connector relative to the assurance device.

16 Claims, 10 Drawing Sheets

Related U.S. Application Data (60) Provisional application No. 61/139,325, filed on Dec. 19, 2008.

(51) Int. Cl.
*A61M 39/10* (2006.01)
*A61M 39/16* (2006.01)

(58) Field of Classification Search
USPC ........ 604/6.16, 244, 247–251, 283, 533–538
See application file for complete search history.

(56) References Cited

U.S. PATENT DOCUMENTS

| | | | |
|---|---|---|---|
| 3,628,813 A | 12/1971 | Lee, Jr. et al. | |
| 4,037,599 A | 7/1977 | Raulerson | |
| 4,340,052 A | 7/1982 | Dennehey et al. | |
| 4,405,312 A * | 9/1983 | Gross | A61L 2/18 604/29 |
| D271,904 S | 12/1983 | Tucker | |
| 4,432,759 A | 2/1984 | Gross et al. | |
| 4,473,369 A | 9/1984 | Lueders et al. | |
| 4,493,708 A | 1/1985 | Sugisawa | |
| 4,539,003 A | 9/1985 | Tucker | |
| 4,596,571 A | 6/1986 | Bellotti et al. | |
| 4,631,056 A | 12/1986 | Dye | |
| 4,723,948 A | 2/1988 | Clark et al. | |
| 4,744,788 A | 5/1988 | Mercer, Jr. | |
| 4,795,197 A | 1/1989 | Kaminski et al. | |
| 4,801,296 A | 1/1989 | Vaillancourt | |
| 5,037,405 A | 8/1991 | Crosby | |
| 5,259,650 A | 11/1993 | Gnauert et al. | |
| 5,380,301 A | 1/1995 | Prichard et al. | |
| 5,531,695 A | 7/1996 | Swisher | |
| 5,957,894 A | 9/1999 | Kerwin et al. | |
| 6,099,519 A | 8/2000 | Olsen et al. | |
| 6,132,405 A | 10/2000 | Nilsson et al. | |
| 6,217,564 B1 | 4/2001 | Peters et al. | |
| D465,843 S | 11/2002 | Guala | |
| D467,339 S | 12/2002 | Trask et al. | |
| 6,508,807 B1 * | 1/2003 | Peters | A61M 39/1011 604/533 |
| D484,592 S | 12/2003 | Ryhman et al. | |
| 6,719,772 B2 | 4/2004 | Trask et al. | |
| 6,783,520 B1 | 8/2004 | Candray et al. | |
| 6,916,051 B2 | 7/2005 | Fisher | |
| 6,936,058 B2 | 8/2005 | Forde et al. | |
| D536,958 S | 2/2007 | Ruhlander | |
| 7,220,241 B2 | 5/2007 | Csincsura et al. | |
| 7,220,242 B2 | 5/2007 | Putter et al. | |
| 7,261,708 B2 | 8/2007 | Raulerson | |
| 7,350,834 B2 | 4/2008 | Ryhman et al. | |
| 2004/0183305 A1 | 9/2004 | Fisher | |
| 2006/0173395 A1 | 8/2006 | Brugger et al. | |
| 2006/0195066 A1 | 8/2006 | Cross | |
| 2007/0088329 A1 | 4/2007 | Bierman | |
| 2008/0009832 A1 | 1/2008 | Barron et al. | |
| 2008/0172039 A1 | 7/2008 | Raines | |
| 2008/0228172 A1 | 9/2008 | Petry | |

FOREIGN PATENT DOCUMENTS

| | | |
|---|---|---|
| EP | 1481185 | 2/2006 |
| EP | 1807140 | 7/2007 |
| GB | 2178811 | 2/1987 |
| JP | 10-026342 | 1/1998 |
| JP | 10-54488 | 2/1998 |
| JP | 2005-264985 | 9/2005 |
| WO | 85/05040 | 11/1985 |
| WO | 91/07206 | 5/1991 |

OTHER PUBLICATIONS

Mexican Office Action for Mexican Application No. MX/a/2011/006613, dated Aug. 12, 2013.
Written Opinion for International Application No. PCT/US2009/068760, dated Mar. 24, 2010.
Japanese Office Action for Japanese Application No. 2011-542491, dated Nov. 25, 2013.
Canadian Office Action dated Nov. 24, 2015 for corresponding Canadian Appln. No. 2,747,510, (3 pages).

* cited by examiner

CATHETER/FISTULA NEEDLE TO BLOODLINE CONNECTION ASSURANCE DEVICE

PRIORITY CLAIM

This application is a divisional of U.S. application Ser. No. 12/640,696, now U.S. Pat. No. 8,603,022, filed Dec. 17, 2009, which claims the benefit of U.S. application Ser. No. 61/139,325 filed Dec. 19, 2008, the entire contents of each of which are hereby incorporated by reference and relied upon.

BACKGROUND

The present disclosure relates to securing and strengthening a connection between an extension tube end of a catheter or fistula needle (device gaining access to a patient's vein) and a bloodline (running to a blood treatment machine).

Catheters and fistula needles used with a blood treatment machine typically have two connectors, one for attachment to a venous bloodline and the other for attachment to an arterial bloodline; the venous and arterial bloodlines attached then being to the blood treatment machine. While the catheter and fistula needle connecters can be provided in a variety of shapes and sizes, the connectors are typically female luer connector. The distal end (with respect to the blood treatment machine) of each of the venous and arterial bloodlines includes a bloodline connector having a male luer, which connects to respective catheter or fistula needle connectors, or female luer connectors.

A disconnection or failure of the connection of such bloodline connectors and catheter or fistula needle connectors while a patient is connected to a blood treatment machine for treatment can cause serious blood loss. A need therefore exists for a device that prevents the bloodlines from coming free from the catheter or fistula needle during treatment, for example, if tension is applied inadvertently to the bloodline.

The most commonly used method to date for securing a catheter or fistula needle to a bloodline for treatment is tape. Tape is wrapped around the connection and then secured to a patient's skin. However, many patients are irritated by the tape and will remove it from their skin, or will not even apply tape to the connection or their skin to begin with, placing them at risk of accidental disconnection. Accordingly, another need exists for the device is that it eliminates the need for tape.

As mentioned above, catheter and fistula needle connecters, while typically being female luer connectors, are provided in a variety of shapes and sizes by a variety of manufacturers. Thus, a further need also exists for the device to be compatible with the variety of industry catheter and fistula needle connectors.

SUMMARY

In general, multiple embodiments of a catheter fistula to bloodline connection assurance device ("assurance device"), which secures and strengthens a connection between an extension tube end of a catheter or fistula needle and a bloodline are provided herein. The assurance device secures both catheter and fistula needle types of patient access. For convenience, the present disclosure may only refer to one of either a catheter or fistula needle. It should be appreciated however that in such instances, the present disclosure refers to both a catheter and fistula needle unless specified otherwise.

A first primary embodiment of the assurance device is configured to be compatible with any industrial catheter/fistula needle female luer connector and is specifically configured for use with a bloodline connector having locking clips that are biased slightly outwardly from the bloodline connector.

The first embodiment of the assurance device is generally cylindrical and includes clamshell halves that open rotatably about at least one hinge. The first embodiment of the assurance device includes a barbed portion (the barbed end of the assurance device being the bloodline-to-machine end) and a luer housing portion (the luer end of the assurance device being the patient access end). Each of the barbed and luer portions includes a closing clip positioned at the open outer or non-hinged side of the respective clamshell halves. Each closing clip includes a male element and a female element, which lock together to hold the assurance device closed when closed about the mated bloodline and patient access luer connectors. A user opens the Assurance Device by manually disengaging the male elements from their respective female elements.

The catheter/fistula needle or patient access end of the first embodiment of the assurance device defines an opening that accommodates an extension tube of any suitable industrial catheter or fistula needle. The bloodline end of the assurance device is left open, such that in one implementation, there is no end wall or surface extending inwardly from the clamshell halves at the far bloodline end. The open end accommodates the bloodline connector locking clips.

Each of the assurance device embodiments is made of a suitable plastic, which does not need to be approved for contact with medical fluids. A more rigid polymer, such as polycarbonate may be desirable.

The first embodiment of the assurance device makes use of the locking clips on the bloodline connector. The interior wall of the barbed portion of the clamshell halves defines a plurality of barbs that are configured to engage with the distal or moveable ends of the locking clips. Each locking clip is biased slightly outwardly to fit between two respective barbs. The barbs are spaced as close together as possible to prevent any axial movement of the bloodline connector when the assurance device is engaged about the mated connectors.

The interior wall of the luer housing portion does not define barbs and instead has a diameter that is large enough to house any suitable industrial catheter/fistula needle female luer connector.

After a user connects the catheter or fistula needle to the bloodline, the user places the connected catheter connector and bloodline connector into the assurance device, which when closed, locks the barbs onto the slightly outwardly biased locking clips of the bloodline connector. The locking prevents axial movement of the bloodline connector relative to the Assurance Device.

Accordingly, in the first embodiment, a connection assurance device for securing a connection of a mated patient-end connector and bloodline connector can includes a cylindrical housing defined by a first half rotatably connected to a second half, the cylindrical housing having a first portion, an inside wall of the first portion defining a plurality of barbs configured to engage with a distal end of a clip which is biased outwardly from the bloodline connector, to prevent axial movement of the bloodline connector relative to the connection assurance device when the cylindrical housing is engaged about the mated patient-end connector and bloodline connector, and a second portion, the second portion configured to accommodate the patient-end connector; and at least one closing mechanism for releasably securing the first half of the cylindrical housing to the second half of the cylindrical housing.

The patient-end connector can be a connector of an extension tube of a device selected from the group consisting of: a catheter and a fistula needle. The at least one closing mechanism can include a clip having a male element and a female element. In an embodiment, when the cylindrical housing is engaged about the mated patient-end connector and bloodline connector, the distal end of the clip is engaged between two of the plurality of barbs. The two clips can be biased outwardly from the bloodline connector and engage with the plurality of barbs. In an embodiment, the patient end connector includes a female luer receiver and the bloodline connector includes a male luer. Further, luer portion can be configured to accommodate a plurality of shapes of patient-end connectors when the cylindrical housing is engaged about the mated patient-end connector and bloodline connector.

A second primary embodiment of the Assurance Device is also configured to be compatible with any suitable industrial catheter/fistula needle connector. The second embodiment includes internal and external clamshells. Internal clamshell halves (could be hinged) pressure seal to the bloodline connector, and form outwardly extending barbs.

The external clamshell opens rotatably about at least one hinge and includes inwardly facing threads that catch the outer barbs of the internal clamshell. The outer clamshell also defines a housing that accommodates any industrial catheter/fistula connector. The external clamshell includes a closing clip similar to the closing clip of the first embodiment of the assurance device.

The catheter/fistula needle end of the external clamshell defines an opening that accommodates an extension tube of any industrial catheter or fistula needle. The bloodline end of the external clamshell is left open, just as in the first embodiment of the assurance device to accommodate a desired bloodline connector. It should be appreciated however that the second embodiment does not require the bloodline connector to have the locking clips as does the first embodiment.

After a user connects the catheter or fistula needle to the bloodline, the user closes the internal clamshell about the bloodline connector. Then, the user closes the external clamshell about the internal clamshell, causing the inwardly facing barbs of the external clamshell to engage the outwardly facing barbs of the internal clamshell. Such engagement prevents axial movement of the bloodline connector (engaged by the internal clamshell halves) relative to the external clamshell.

Accordingly, in the second primary embodiment, a connection assurance device for securing a connection of a mated patient-end connector and bloodline connector can comprise an external cylindrical housing defined by a first half rotatably connected to a second half, an inner wall of the external cylindrical housing including a plurality of inwardly extending barbs; an internal cylindrical housing defined by a first half and a second half each configured to engage about the bloodline connector, an outer wall of the internal cylindrical housing including a plurality of outwardly extending threads configured to engage with the plurality of inwardly extending barbs of the external cylindrical housing when the external cylindrical housing is engaged about the internal cylindrical housing; and at least one closing mechanism for releasably securing the first half of the external cylindrical housing to the second half of the external cylindrical housing.

The patient-end connector can be a connector of an extension tube of a device selected from the group consisting of: a catheter and a fistula needle. The at least one closing mechanism can include a clip having a male element and a female element. An inner wall of the internal cylindrical housing can define a cavity configured to engage an outwardly extending portion of the bloodline connector. In an embodiment, the patient end connector includes a female luer receiver and the bloodline connector includes a male luer. The connection assurance is again compatible with a plurality of shapes of patient-end connectors. In an embodiment, the first half of the internal cylindrical housing is rotatably connected to the second half of the internal cylindrical housing.

A third primary embodiment of the assurance device is also configured to be compatible with any suitable industrial catheter/fistula needle connector. The third embodiment of the assurance device includes a clamshell having two halves that open rotatably about at least one hinge. The assurance device includes a male luer portion that pressure seals to the male luer portion of the bloodline connector. The bloodline male luer portion of the device extends to a female luer portion, which is lined with a compressible material that conforms around any industrial catheter/fistula needle connector when the assurance device is closed about the mated connectors. The third embodiment of the assurance device includes closing clips similar to those in the first and second embodiments.

The catheter end of the third embodiment of the assurance device defines an opening that accommodates any industrial catheter or fistula female luer connector. The bloodline end defines an opening that accommodates the bloodline connector, which as with the second embodiment may or may not include locking clips.

After a user connects the catheter to the bloodline, the user positions the male luer portion of the third embodiment of the assurance device into engagement with the male luer of the bloodline connector. Once the assurance device is closed, this prevents axial movement of the bloodline connector relative to the assurance device. The female luer is accordingly positioned along the compressible material in the female luer portion of the third embodiment of the assurance device, causing the compressible material to conform about the female luer when the assurance device is closed about the mated connectors, and preventing both axial and rotational movement of the female luer connector relative to the assurance device.

Accordingly, the third primary embodiment of the connection assurance device for securing a connection of a mated patient-end connector and bloodline connector can include a cylindrical housing defined by a first half rotatably connected to a second half, the cylindrical housing having: a first portion defined by the cylindrical housing, the first portion configured to engage the bloodline connector when the cylindrical housing is engaged about the mated patient-end connector and bloodline connector, and a second portion defined by the cylindrical housing, the second portion including a compressible material extending inward from an inner wall of the lower portion, the compressible material configured to conform about the patient-end connector when the cylindrical housing is engaged about the mated patient-end connector and bloodline connector; and at least one closing mechanism for releasably securing the first half of the cylindrical housing to the second half of the cylindrical housing.

The patient-end connector can be a connector of an extension tube of a device selected from the group consisting of: a catheter and a fistula needle. The at least one closing mechanism can include a clip having a male element and a female element. The compressible material can be a sponge-like material, and memory foam or be configured to absorb a fluid. An inner wall of the first portion can define a cavity configured to engage an outwardly extending portion of the bloodline connector. The second portion can be configured to accommodate a plurality of shapes of patient-end connectors when the cylindrical housing is engaged about the mated patient-end connector and bloodline connector.

It is accordingly an advantage of the present discloser to secure a machine tube to a patient access tube to increase safety during an extracorporeal treatment, which may be performed at home.

Additional features and advantages are described herein, and will be apparent from the following Detailed Description and the figures.

DETAILED DESCRIPTION

Figure 1:
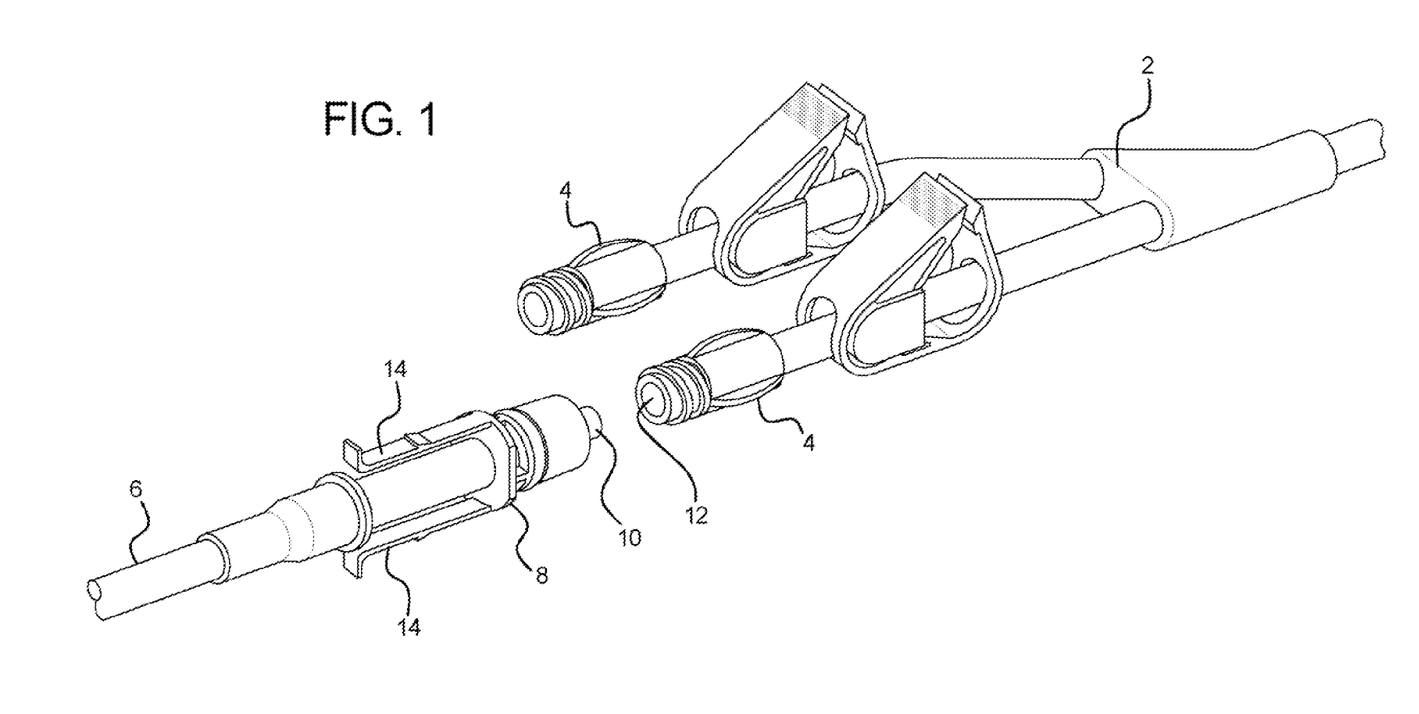
FIG. 1 is a perspective view of a distal end (with respect to a blood treatment machine) of a bloodline having a bloodline connector including a male luer, and the extension tubes of a catheter or fistula needle, each of the extension tubes including a female luer connector.

Referring now to the drawings and in particular to FIG. 1, each embodiment of the assurance device discussed herein secures and strengthens a connection between an extension tube end of a catheter or fistula needle (device gaining access to a patient's vein) and a bloodline (running to a blood treatment machine). FIG. 1 shows an example of a catheter 2 having two connectors 4, one for attachment to a venous bloodline and the other for attachment to an arterial bloodline. While the connecters 4 may be provided in a variety of shapes and sizes, each of connectors 4 is a female luer connector in one preferred embodiment.

FIG. 1 also illustrates an example of a distal end (with respect to blood treatment machine) of a bloodline 6 and a bloodline connector 8, which connects to catheter connector 4, or female luer connector. The bloodline connector 8 accordingly includes a male luer 10 housed in an internally threaded cavity that engages with the female luer receiver 12 of the catheter connector 4. The bloodline connector 8 in FIG. 1 includes two spring-like locking clips 14 that extend externally from the bloodline connector 8. The locking clips 14 attach the distal end of the bloodline 6 to the machine (not shown) in certain instances, such as for priming and rinse-back.

Figure 2:
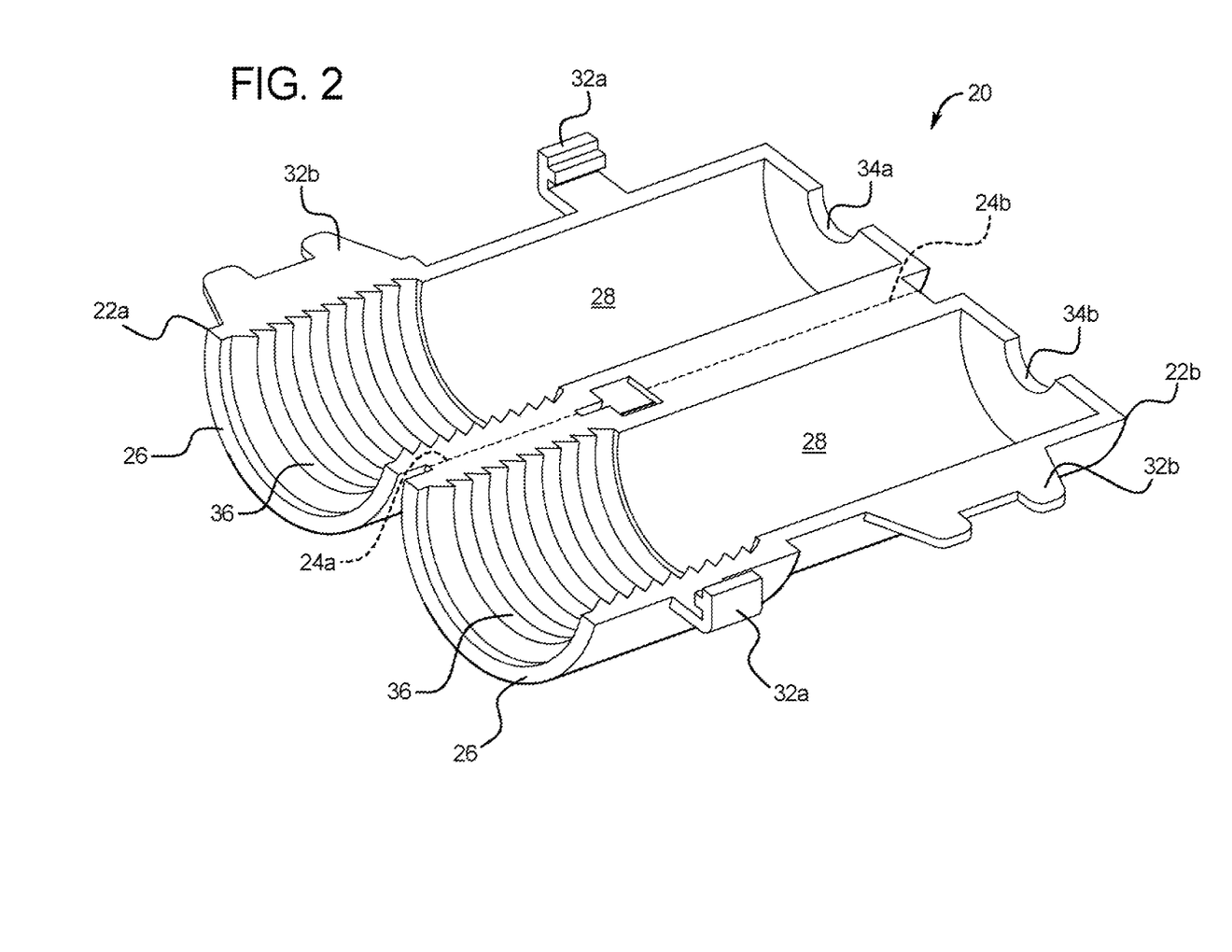
FIG. 2 is a perspective view of a first embodiment of the assurance device.
Figure 3:
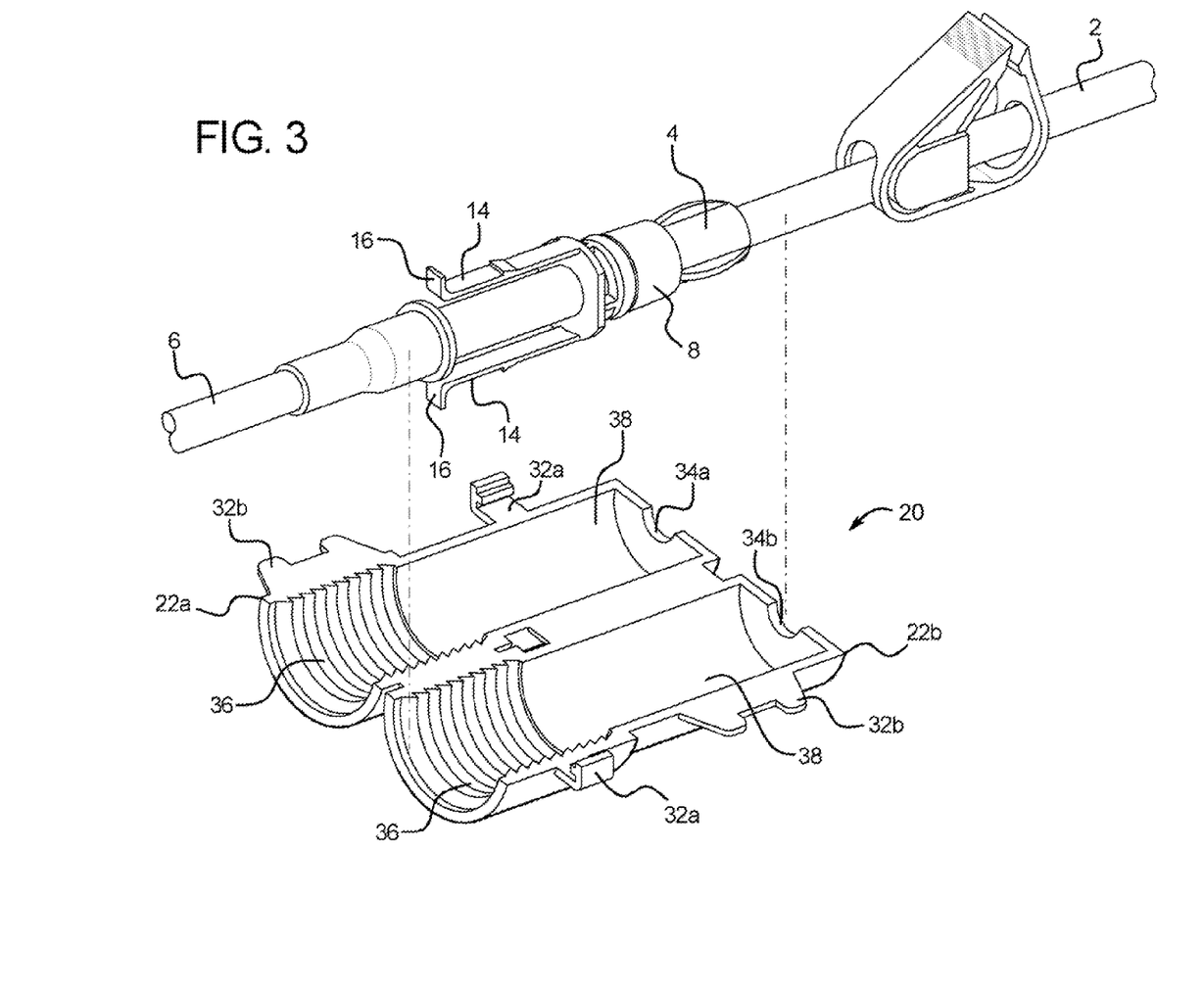
FIG. 3 is an exploded perspective view of the first embodiment of the assurance device in relation to a mated bloodline connector and catheter or fistula needle connector.
Figure 4:
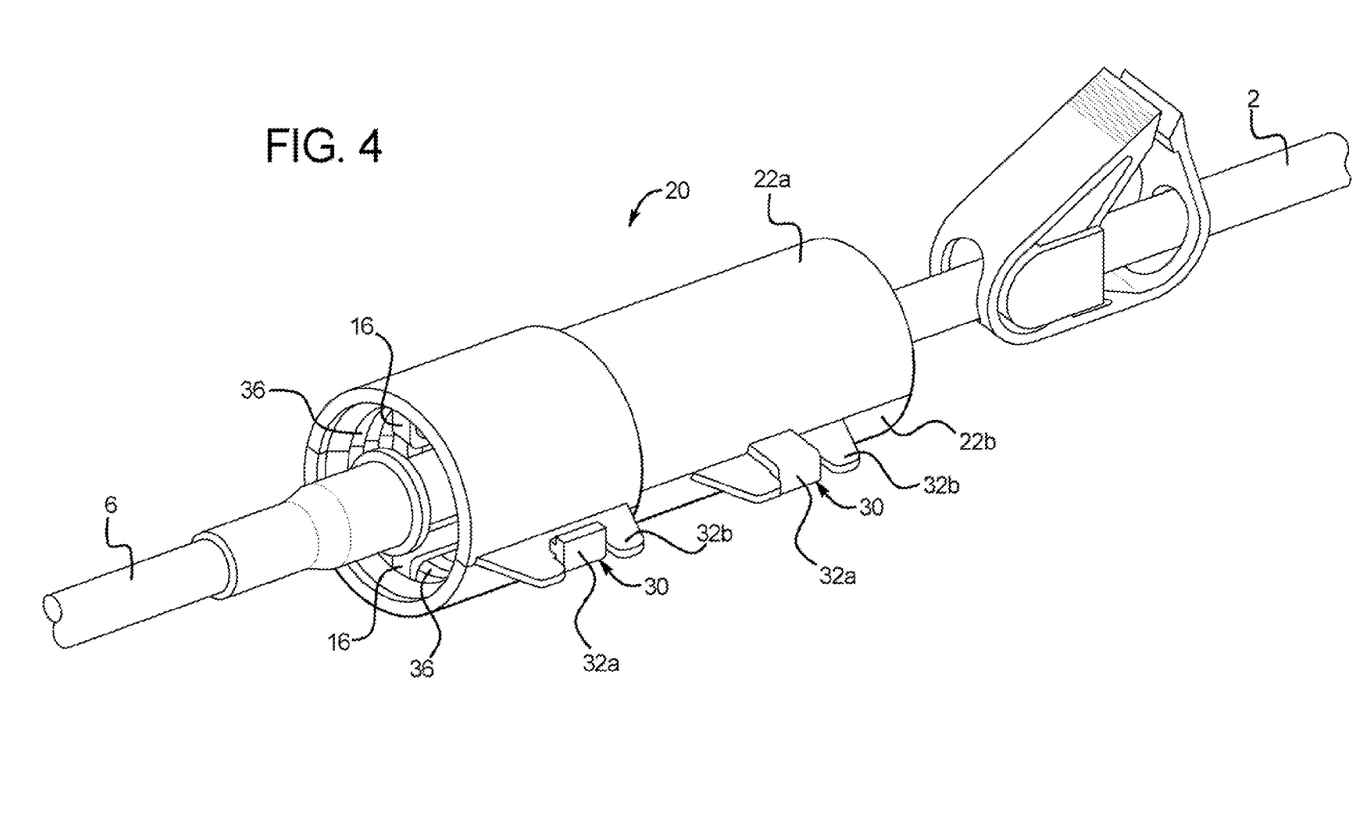
FIG. 4 is a perspective view of the first embodiment of the assurance device in a closed position about a mated bloodline connector and catheter or fistula needle connector.

Referring now to FIGS. 2 to 4, a first primary embodiment of the assurance device is illustrated by device 20, which is compatible with any industrial suitable catheter/fistula needle female luer connector and is specifically configured for use with the bloodline connector 8 having spring-like locking clips 14 shown in FIG. 1, or a similar bloodline connector.

Referring to FIGS. 2 to 4, assurance device 20 is at least substantially cylindrical and includes clamshell halves 22a and 22b that open rotatably about hinges 24a and 24b. It should be appreciated that in various embodiments, the assurance device 20 may include a single hinge or multiple hinges. Halves 22a and 22b of the assurance device 20 may alternatively be free from each other.

Assurance device 20 includes a barbed portion 26 and a luer housing portion 28. Each of barbed portion 26 and luer portion 28 includes a closing clip 30 (FIG. 4) positioned at the open outer or non-hinged side of the clamshell halves 22a and 22b. Each closing clip 30 includes a male element 32a and a female element 32b, which lock together to hold the assurance device 20 closed when the device is closed about the mated luer connectors 4 and 8. A user opens the assurance device 20 by manually disengaging the male elements 32a from their respective female elements 32b.

It should be appreciated that in various embodiments, the assurance device 20 may include a single closing clip 30 or other desirable number of closing clips. Closing clip alternatively or additionally includes snap-fitting elements assurance devices could be held together using a loop and pile (Velcro) tape releasable fastener.

The catheter end of the assurance device 20 defines an opening formed from opening portions 34a and 34b defined by respective the clamshell halves 22a and 22b. The opening 34a/34b accommodates any industrial suitable catheter or fistula needle extension tube, such as those of catheter 2 in FIG. 1. The bloodline end of the Assurance Device 20 is left open to accommodate the bloodline connector 8, as seen in FIG. 4.

As seen best in FIGS. 3 and 4, the first embodiment of the assurance device 20 makes use of the spring-like locking clips 14 of bloodline connector 8. The interior wall of the barbed portion of the clamshell halves 22a and 22b defines a plurality of barbs 36 that are configured to engage with the distal or moveable ends 16 of the locking clips 14. Each spring-like locking clip 14 is biased slightly outwardly to cause the distal or moveable ends 16 to fit between two respective barbs 36. The barbs 36 are spaced as close together as possible to prevent any axial movement of the bloodline connector 8 when the assurance device 20 is engaged about the mated connectors 4 and 8.

The interior wall 38 of the luer housing portion 28 does not define barbs and has a diameter that is large enough to house any suitable industrial catheter/fistula needle connector, such as connector 4 illustrated in FIG. 1.

As seen in FIGS. 3 and 4, after a user connects the catheter or fistula needle 2 to the bloodline 6, the user places the connected catheter connector 4 and bloodline connector 8 into the assurance device 20, which when closed, locks barbs 36 onto the moveable ends 16 of the slightly outwardly biased locking clips 14 of the bloodline connector 8.

Figure 5:
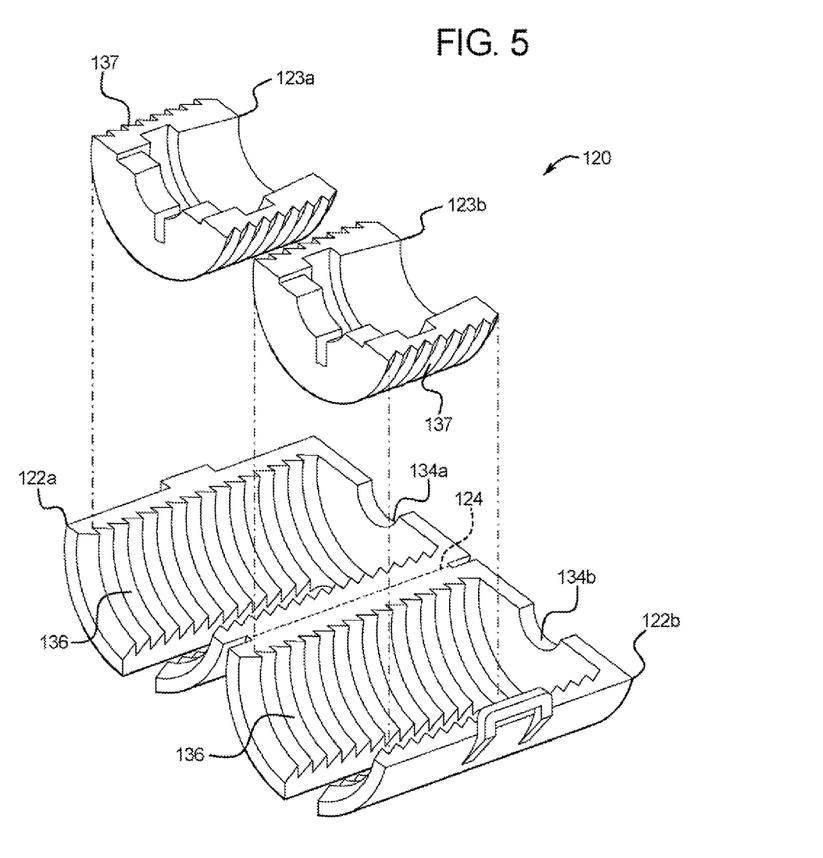
FIG. 5 is an exploded perspective view of a second embodiment of the assurance device.
Figure 6:
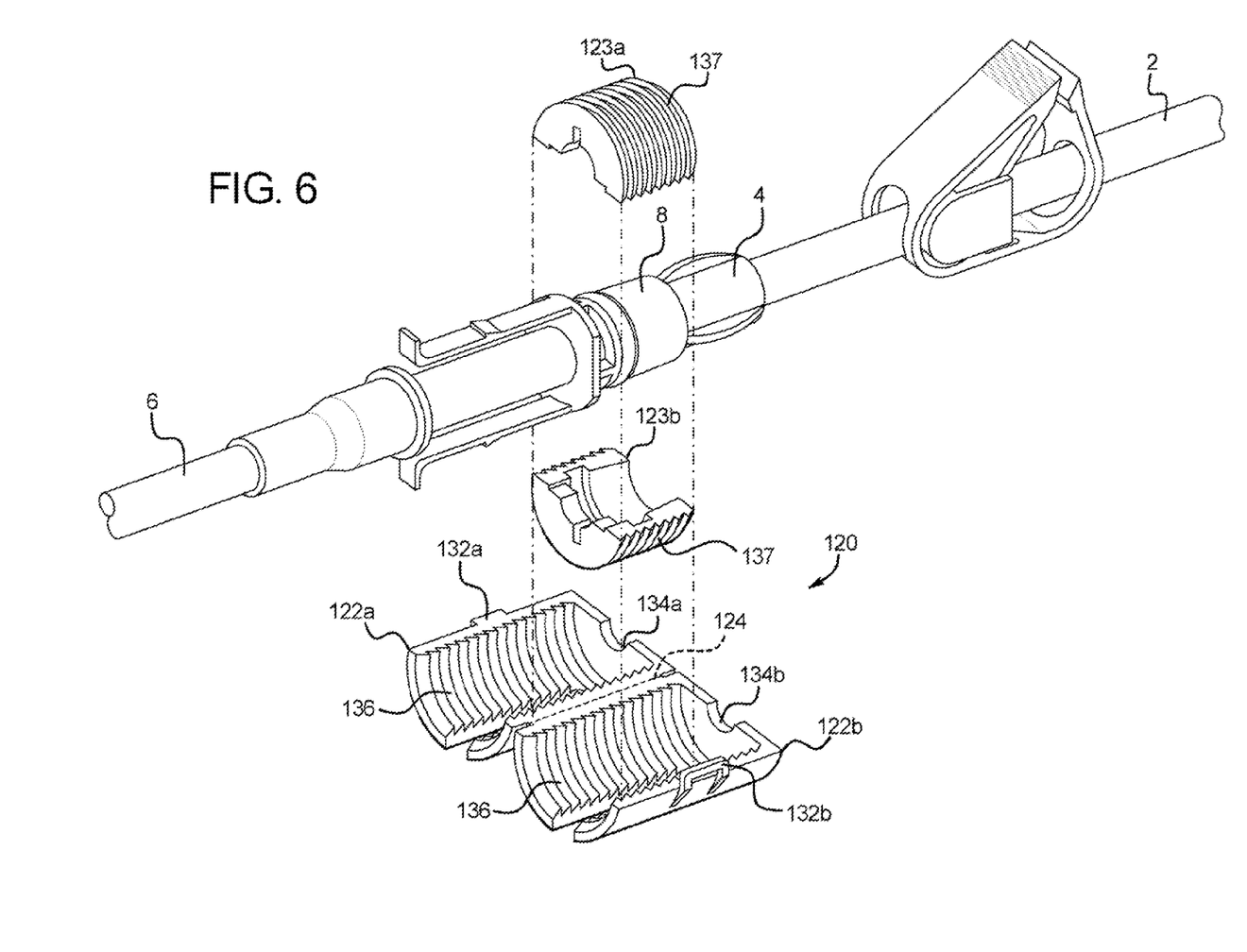
FIG. 6 is an exploded perspective view of the second embodiment of the assurance device in relation to a mated bloodline connector and catheter or fistula needle connector.
Figure 7:
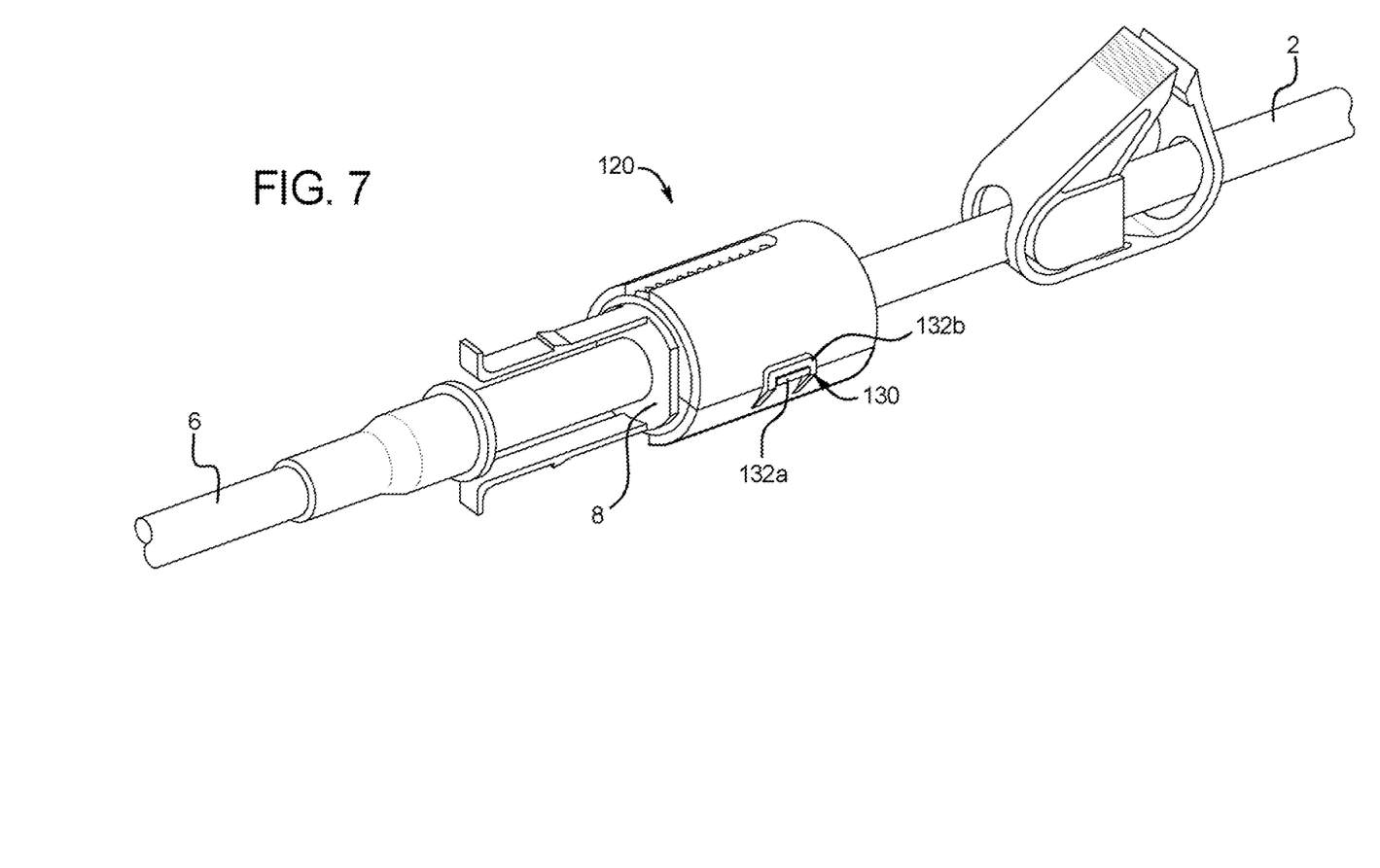
FIG. 7 is a perspective view of the second embodiment of the assurance device in a closed position about a mated bloodline connector and catheter or fistula needle connector.

Referring now to FIGS. 5 to 7, a second primary embodiment of the assurance device is illustrated by assurance device 120, which is configured to be compatible with any suitable industrial catheter/fistula needle connector and is specifically configured for use with the bloodline connector 8 or a similar bloodline connector.

Assurance device 120 includes internal and external clamshells. Internal clamshell halves 123a and 123b pressure seal to bloodline connector 8 and form outwardly extending barbs 137. In an alternative embodiment, internal clamshell halves 123a and 123b are hinged together and hingedly close about bloodline connector 8.

External clamshell halves 122a and 122b rotatably open about hinge 124 and include inwardly facing threads 136 that catch or lock onto outer barbs 137 of the inner clamshell halves 123a and 123b. The outer clamshell halves 122a and 122b also define a housing that accommodates any suitable industrial catheter/fistula connector.

Assurance device 120 includes a closing clip 130 (FIG. 7) positioned at the open outer or non-hinged side of the external clamshell halves 122a and 122b. Closing clip 130 includes a male element 132a and a female element 132b, which lock together to hold the assurance device 120 closed when closed about the mated luer connectors 4 and 8. A user opens the assurance device 120 by manually disengaging the male element 132a from the respective female element 132b. Any alternatives discussed above for locking clip 30 is also applicable to closing clip 130.

The catheter end of the external clamshell defines an opening formed of opening portions 134a and 134b defined by respective clamshell halves 122a and 122b. Opening 134a/134b accommodates tube extending off of any suitable industrial catheter or fistula needle, such as those of catheter 2 in FIG. 1. The bloodline end of the external clamshell is left open to accommodate the bloodline connector 8, as seen in FIGS. 6 and 7.

Referring to FIGS. 6 and 7, after a user connects the catheter or fistula needle 2 to the bloodline 6, the user pressure fits the internal clamshell halves 123a and 123b about the bloodline connector 8. Then, the user closes the external clamshell halves 122a and 122b about the internal clamshell halves 123a and 123b, causing the inwardly facing barbs 136 of the external clamshell halves 122a and 122b to engage the outwardly facing barbs 137 extending from the internal clamshell halves 123a and 123b.

Figure 8:
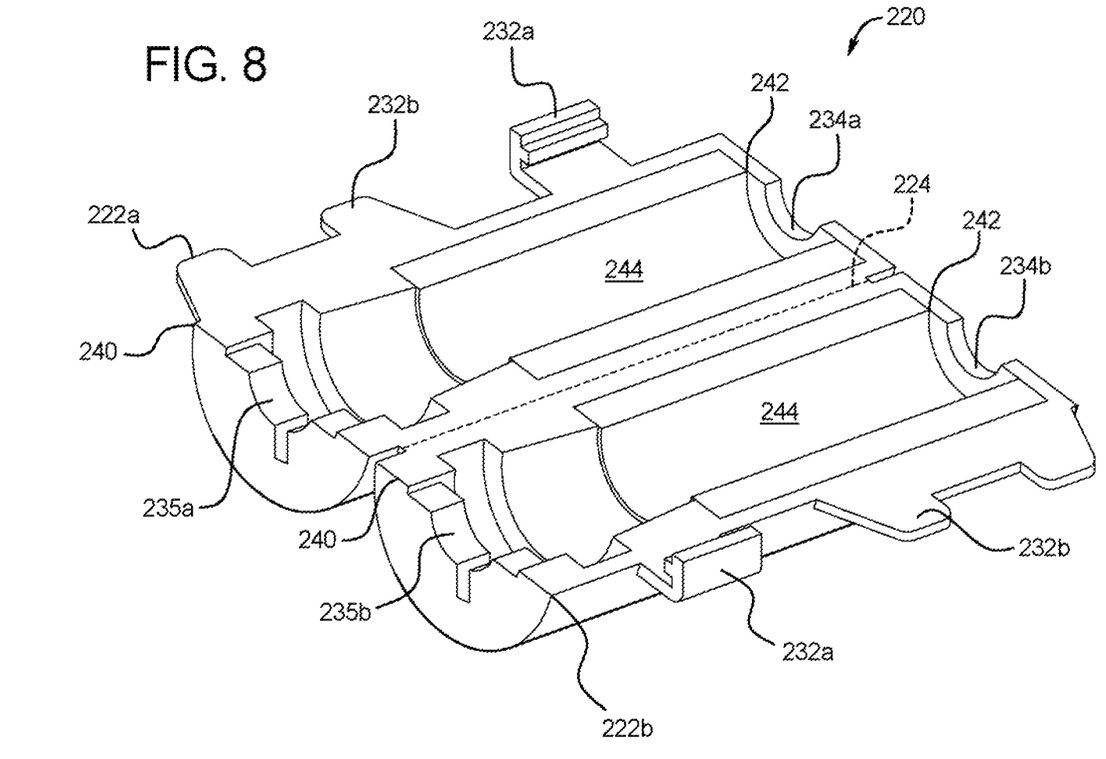
FIG. 8 is an exploded perspective view of a third embodiment of the assurance device.
Figure 9:
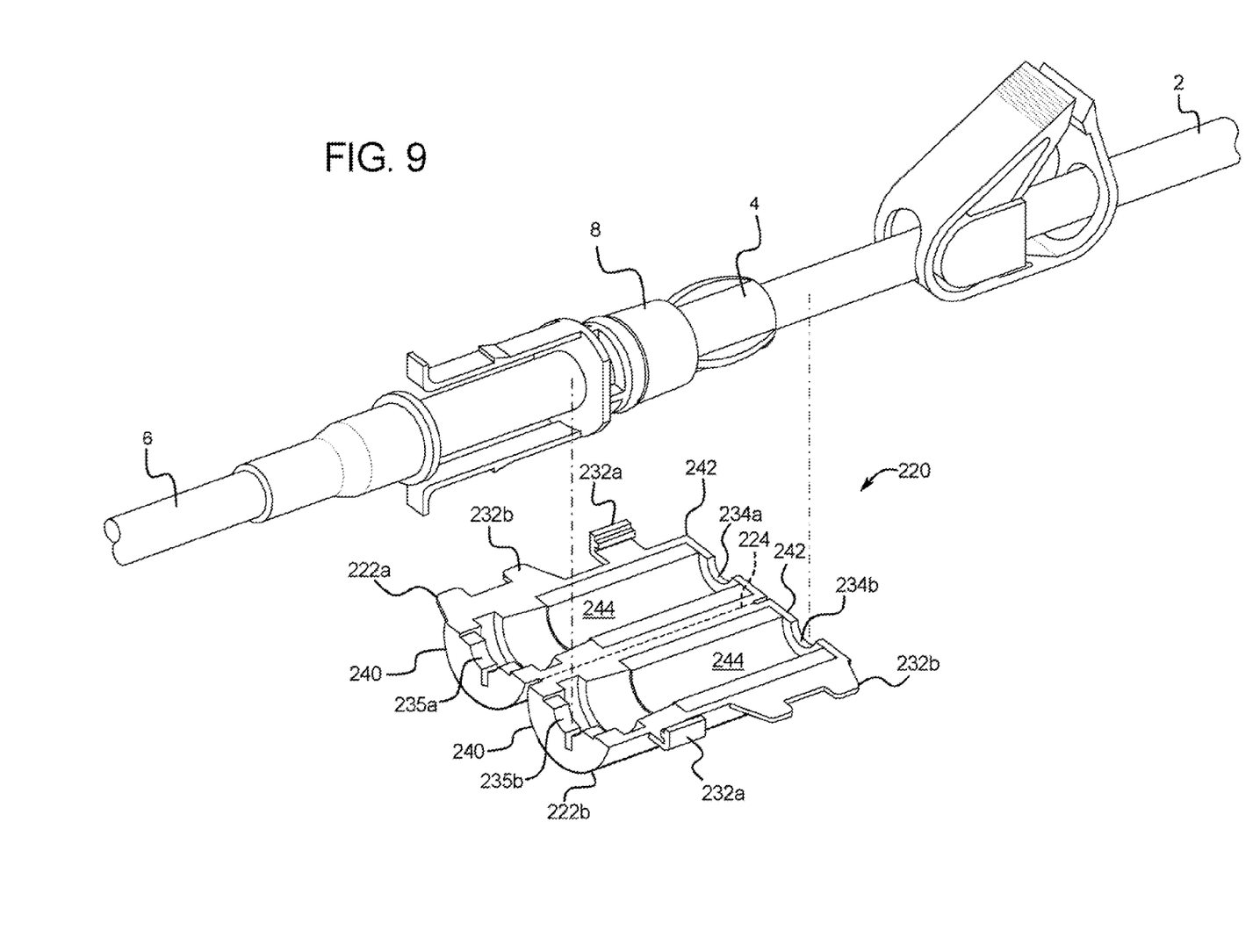
FIG. 9 is an exploded perspective view of the third embodiment of the assurance device in relation to a mated bloodline connector and catheter or fistula needle connector.
Figure 10:
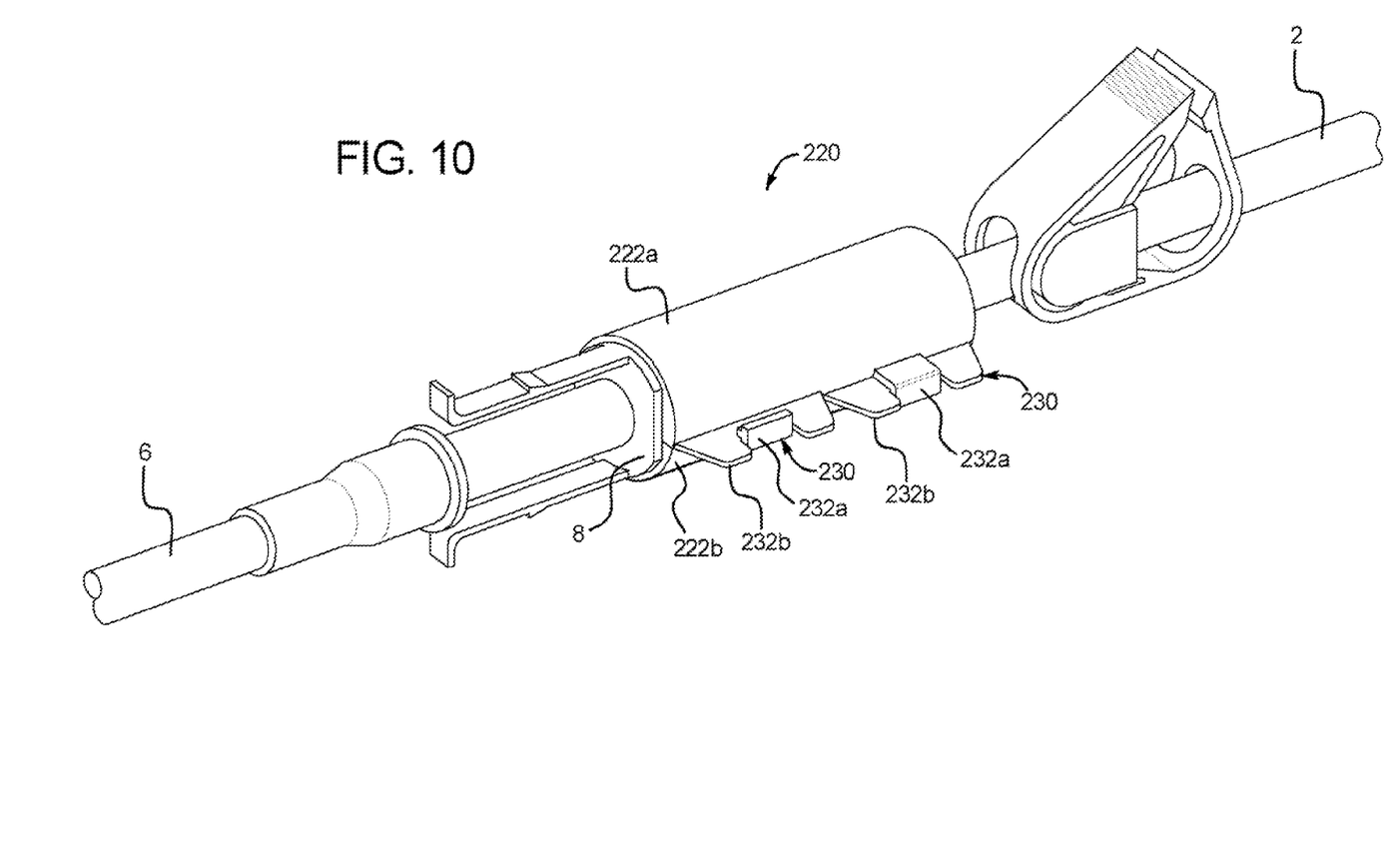
FIG. 10 is a perspective view of the third embodiment of the assurance device in a closed position about a mated bloodline connector and catheter or fistula needle connector.

Referring now to FIGS. 8 to 10, a third primary embodiment of the assurance device is illustrated by assurance device 220, which is compatible with any suitable industrial catheter/fistula needle connector and is specifically configured for use with the bloodline connector 8 or a similar bloodline connector. It should be noted that blood line connectors 8 may, but do not have to, include spring-line clips 14 discussed above for either assurance device 120 or 220.

As best illustrated in FIG. 8, assurance device 220 includes a clamshell having two halves 222a and 222b that open rotatably about hinge 224. It should be appreciated that although FIGS. 8 and 9 illustrate the clamshell halves 222a and 222b having one hinge 224, the clamshell halves 222a and 222b may be attached by a single hinge or other desired number of hinges or may be separate pieces.

Assurance device 220 includes a male luer portion 240 that pressure seals to bloodline connector 8. Male luer portion 240 extends to a female luer housing portion 242, which is lined with a compressible material 244 that conforms around any suitable industrial catheter/fistula needle connector when the assurance device 220 is closed about the mated connectors. Material 244 is in one embodiment a rubber, sponge rubber, or memory foam having a relatively high coefficient of friction. Silicone or neoprene may be suitable materials. Material 244 is adhered to female luer portion 242 in one embodiment. Material 244, e.g., if sponge-like, also provides the added benefit of absorbing fluid or blood in the event of luer disconnection. Frictional material 244 also prevents rotation of the catheter/fistula needle female luer connector 4 within device 220 and relative to the bloodline connector 8.

Each of the male luer portion 240 and female luer portion 242 includes a closing clip 230 positioned at the open outer or non-hinged side of the clamshell halves 222a and 222b. Each closing clip 230 includes a male element 232a and a female element 232b, which lock together to hold the assurance device 220 closed when closed about the mated luer connectors 4 and 8. A user opens the assurance device 220 by manually disengaging the male elements 232a from their respective female elements 232b. Closing clip 230 includes any of the alternative embodiments discussed above for clip 30.

The catheter end of the clamshell defines an opening formed from opening portions 234a and 234b located on respective clamshell halves 222a and 222b. Opening 234a/234b accommodates a tube exiting from any suitable industrial catheter or fistula needle, such as those of catheter 2 in FIG. 1. The bloodline end of the assurance device 220 defines an opening formed from opening portions 235a and 235b located on respective clamshell halves 222a and 222b. Opening 235a/235b accommodates bloodline connector 8.

As seen in FIGS. 9 and 10, after a user connects the catheter to the bloodline, the user positions the upper portion of the assurance device 220 in engagement with the bloodline connector 8. The female luer connector 4 is accordingly positioned along the compressible material in the female luer portion 238 of the assurance device 220, which causes compressible material 244 to squeeze to and conform about the female luer connector 4 when the assurance device 220 is closed about the mated connectors 4 and 8. Again, device 200 is advantageous in one respect because it confines female luer connector 4 movement both axially and rotationally.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A connection assurance device for securing a connection of a patient-end connector to a bloodline connector, the connection assurance device comprising:
   a cylindrical housing including a first half mated to a second half, the cylindrical housing including a first portion configured to engage the bloodline connector when the cylindrical housing is engaged about the mated patient-end connector and bloodline connector, and a second portion including a compressible material extending inwardly from an inner wall of the second portion, the compressible material configured to squeeze to and conform only about the patient-end connector when the cylindrical housing is engaged about the mated patient-end connector and bloodline connector; and at least one closing mechanism for releasably securing the first half of the cylindrical housing to the second half of the cylindrical housing.

2. The connection assurance device of claim 1, wherein the first half of the cylindrical housing is connected hingedly to the second half of the cylindrical housing.

3. The connection assurance device of claim 1, wherein the at least one closing mechanism comprises a clip provided by the housing, the clip including interlocking male and female elements.

4. The connection assurance device of claim 1, wherein the compressible material is at least one of rubber, a sponge-like material, or memory foam.

5. The connection assurance device of claim 1, wherein the compressible material is configured to absorb a fluid leaking from the mated patient-end connector and bloodline connector.

6. The connection assurance device of claim 1, wherein an inner wall of the first portion defines a cavity configured to engage an outwardly extending feature of the bloodline connector.

7. The connection assurance device of claim 1, wherein the compressible material accommodates a plurality of shapes of patient-end connectors.

8. A connection assurance device for securing a connection of a patient-end connector to a bloodline connector, the connection assurance device comprising:

a housing including a first half mated hingedly to a second half, the housing including a first portion configured to engage the bloodline connector when the housing is engaged about the mated patient-end connector and bloodline connector, and a second portion including a compressible material extending inwardly from an inner wall of the second portion, the compressible material configured to squeeze to and conform only about the patient-end connector when the housing is engaged about the mated patient-end connector and bloodline connector; and at least one closing mechanism for releasably securing the first half of the housing to the second half of the housing.

9. The connection assurance device of claim 8, wherein the housing is cylindrical.

10. The connection assurance device of claim 8, wherein the at least one closing mechanism comprises a clip provided by the housing, the clip including interlocking male and female elements.

11. The connection assurance device of claim 8, wherein the compressible material is at least one of rubber, a sponge-like material, memory foam, or configured to absorb a fluid.

12. The connection assurance device of claim 8, wherein the compressible material accommodates a plurality of shapes of patient-end connectors.

13. The connection assurance device of claim 8, wherein an inner wall of the first portion defines a cavity configured to engage an outwardly extending feature of the bloodline connector.

14. A connection assurance device for securing a connection of a patient-end connector to a bloodline connector, the connection assurance device comprising:

a housing including a first half mated hingedly to a second half, the housing including a first portion configured to engage the bloodline connector when the housing is engaged about the mated patient-end connector and bloodline connector, and a second portion including a compressible material extending inwardly from an inner wall of the second portion, the compressible material configured to squeeze to the patient-end connector only and prevent rotation of the patient-end connector relative to the bloodline connector when the housing is engaged about the mated patient-end connector and the bloodline connector; and at least one closing mechanism for releasably securing the first half of the housing to the second half of the housing.

15. The connection assurance device of claim 14, which confines movement of the patient-end connector both axially and rotationally.

16. The connection assurance device of claim 14, wherein the compressible material is sponge-like for absorbing fluid or blood.

* * * * *